(12) United States Patent
McKnight et al.

(10) Patent No.: US 7,938,121 B2
(45) Date of Patent: May 10, 2011

(54) ABDOMINAL RESTRAINT FOR MEDICAL PROCEDURES

(75) Inventors: John McKnight, Morgantown, WV (US); Chi Lam Yau, Dover, NH (US); Mark MacMahon, Portland, ME (US)

(73) Assignee: Merit Medical Systems, Inc., South Jordan, UT (US)

( * ) Notice: Subject to any disclaimer, the term of this patent is extended or adjusted under 35 U.S.C. 154(b) by 1337 days.

(21) Appl. No.: 11/056,044

(22) Filed: Feb. 11, 2005

(65) Prior Publication Data

US 2006/0180158 A1    Aug. 17, 2006

(51) Int. Cl.
*A61G 15/00* (2006.01)

(52) U.S. Cl. ............................................. 128/845

(58) Field of Classification Search .................. 128/869, 128/870, 846, 876, 845; 5/601, 621
See application file for complete search history.

(56) References Cited

U.S. PATENT DOCUMENTS

| | | | |
|---|---|---|---|
| 3,861,666 A * | 1/1975 | Nishiyama et al. | 5/601 |
| 4,655,206 A * | 4/1987 | Moody | 5/628 |
| 5,048,541 A * | 9/1991 | Haneline | 128/876 |
| 5,709,220 A * | 1/1998 | Kellan | 128/849 |
| 6,357,066 B1 * | 3/2002 | Pierce | 5/710 |
| 6,363,936 B1 | 4/2002 | McCormick et al. | |
| 6,938,623 B2 * | 9/2005 | Graupner et al. | 128/869 |

OTHER PUBLICATIONS

Application guidelines flyer for "Max-Support abdominal retraction belt" produced by Vascular Solutions, Inc., ML1482 Jan. 2005 Rev. A, Minneapolis, MN.
International Preliminary Report and Written Opinion for PCT/US2006/005180 dated Feb. 13, 2006.

* cited by examiner

*Primary Examiner* — Patricia M Bianco
*Assistant Examiner* — Camtu T Nguyen
(74) *Attorney, Agent, or Firm* — Stoel Rives LLP

(57) ABSTRACT

The present invention provides an abdominal restraint for use in medical and surgical procedures that is specially adapted for restraining an abdominal pannus and exposing the groin area of a patient. The abdominal restraint of the present invention includes a base member and a support member that is selectively attachable to the base member. Alternatively, the abdominal restraint of the present invention includes a lateral member that is selectively attachable to at least one longitudinal member, which in turn may be attached to an operating or examining table. In its various embodiments, the present invention discloses a number of designs for the safe and efficient restraint of an abdominal pannus.

11 Claims, 7 Drawing Sheets

ABDOMINAL RESTRAINT FOR MEDICAL PROCEDURES

BACKGROUND OF THE INVENTION

1. Field of the Invention

The present invention relates generally to the field of medical and surgical devices, and in particular to the use of external restraining or support means for securing or immobilizing a patient during a medical or surgical procedure.

2. Summary of the State of the Art

Obesity is fast becoming a problem of epidemic proportions in the United States. Aside from the health risks inherent to obesity, the size and constitution of the human body can have effects on the quality of medical care that is provided. Although routine visits to the doctor's office are normally not a cause for alarm, obese patients that are seeking specialty care may be inadvertently hampering their doctors' efforts through their sheer size and shape. A particular problem is encountered for those patients that have developed what is known as an abdominal apron, or pannus.

A pannus is a region of loose skin and fatty tissue in the lower abdomen that, due to its lack of musculature and mass, begins to descend below the abdomen, appearing as an apron. In more severe cases, a pannus will completely obscure the patient's groin area. A pannus is classified by weight, ranging between 5 and 125 pounds (2 to 60 kilograms). A pannus can thus be either a mere inconvenience or a serious obstacle for any doctor that is attempting to examine, treat or otherwise access the groin area of the patient. There are a number of medical and surgical procedures that require access to the groin area, not the least of which are gynecological and urological procedures.

Doctors must also access the patient's groin area for all types of cardiovascular procedures, ranging from angioplasty to any type of thoracic surgery that requires catheterization of the femoral artery. In most cardiovascular procedures, the femoral artery is used for catheterization or, in the case of angioplasty, as a channel through which a stent or other medical device will be guided. It should be apparent that these types of procedures require absolute precision and care, and so the groin region should ideally be clear of any obstacles or interference.

Unfortunately, there is a strong correlation between obesity and the need for medical care, particularly with respect to coronary illnesses. As a person's weight increases, they are simultaneously increasing their risk for heart disease, as well as decreasing the physical accessibility to their groin region through the formation of an abdominal pannus. That is, obese people not only require more medical care, but their obesity renders that medical care more difficult to provide. For example, it is estimated that there are approximately six million catheterization procedures per year in the United States. Ninety-percent of those patients exhibit some form of obesity, ranging from mildly overweight to morbidly obese. In each of these cases, however, the attending physician or surgeon must find a method or means for accessing the groin area through or around the patient's abdominal pannus.

Current operating room procedures for handling a pannus are limited to simple and ineffectual remedies. In some instances, the pannus is restrained using tape or some other adhesive to lift it out of the groin region. This method has proven unreliable, as the skin on the underside of a pannus is typically not sufficiently clean or rigid to maintain its form under the stress of the tape. As a result, the skin is often sloughed off on the tape, releasing the pannus to its resting place over the groin area. Rather than attempt to secure the pannus by tape or adhesive, still other medical professionals are simply proceeding with the procedures around, over, and through the pannus tissues. This practice is fraught with danger, as a large pannus will significantly obscure the doctor's view of any anatomical feature that he or she is seeking, including the femoral artery.

Nevertheless, the current state of the art has been unable to solve the problems noted above. Given the gains in medical technology in the past twenty years, it is also necessary to insure that those technologies can be used to help those who most need them. As such, there is a need in the art for a system or device for restraining an abdominal pannus during medical or surgical procedures.

SUMMARY OF THE INVENTION

Accordingly, the present invention provides an abdominal restraint for use in medical and surgical procedures that is specially adapted for restraining an abdominal pannus and exposing the groin area of a patient. The abdominal restraint of the present invention includes a base member and a support member that is selectively attachable to the base member. In its various embodiments, the base member incorporates a number of features including locking mechanisms for securing the support member, and handles for positioning and securing the base member beneath a prone patient.

The support member of the present invention is generally defined by a pair of flexible bands that border a contoured web. The contoured web is specially shaped for accommodating the shape of an abdominal pannus, particularly of the large variety. As described below, both the flexible bands and the contoured web are preferably hypoallergenic, sterile and non-radio opaque. In addition, the support member must be constructed of a material that is strong enough to leverage and support a very large abdomen. Preferred materials discussed below include nylon and other synthetic materials.

In another embodiment, the abdominal restraint includes a lateral member that is selectively connected to at least one longitudinal member disposed along the length of the patient. The longitudinal members are selectively secured to the operating or examination table, and then the lateral member is disposed about the abdomen of the patient such that it displaces the pannus and exposes the groin area for a medical or surgical procedure. As discussed below, it is preferable for the abdominal restraint to be composed of sterile and hypoallergenic materials for use in surgical environments.

Further details and advantages of the present invention will become readily apparent from the Detailed Description of the Preferred Embodiments that refers specifically to the following drawings.

DETAILED DESCRIPTION OF THE PREFERRED EMBODIMENTS

As described in further detail below, the present invention includes an abdominal restraint for providing a safe and effective means for physicians and surgeons to easily access the groin region of an overweight patient. In its various embodiments, the present invention is usable over a range of patients including those having a high-grade pannus that weighs over 100 pounds or 45 kilograms. Other embodiments of the present invention are well suited for restraining and displacing a smaller abdominal mass, such as a 5 to 15 pound (2 to 6 kilogram) pannus.

Figure 1:
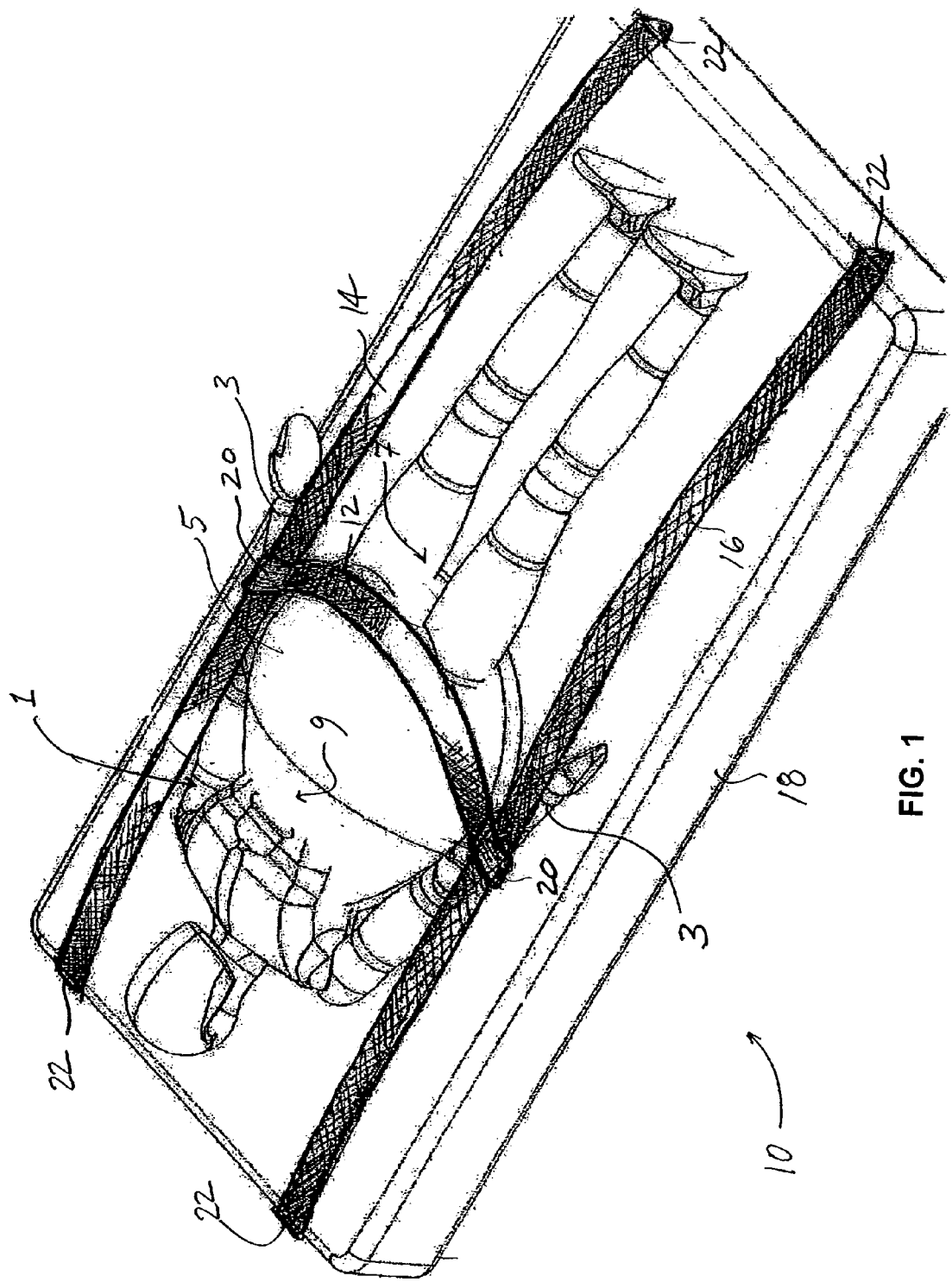
FIG. 1 is a perspective view of an abdominal restraint in accordance with one embodiment of the present invention shown in use on a patient.

Turning now to the figures, one embodiment of an abdominal restraint 10 of the present invention is shown in FIG. 1 from a perspective view in use on a patient 1. For purposes of the following discussion, the patient 1 defines a series of regions or areas, generally designated as an abdominal apron or pannus 5, a groin region 7, and a torso 9. The regions noted should be interpreted to include those areas normally associated with those terms, with the further understanding that the groin area includes the reproductive organs, the inner femoral region including the femoral artery, and any other anatomical structures that may require examination or surgical procedures in the practice of medicine.

As shown in FIG. 1, the patient 1 is laying in a prone position on a table 18, which should be understood to represent an operating or examination table as commonly known in the medical fields. The abdominal restraint 10 is disposed about the patient 1 such that a lateral member 12 is secured about the pannus 5 near the groin area 7. The lateral member 12 is preferably comprised of a synthetic material, such as nylon, that has been sterilized for medicinal purposes. The lateral member 12 is also preferably hypoallergenic, as the skin located on the lower area (groin-side) of the pannus 5 is often very sensitive and easily damaged. As is often the case, the lower area of the pannus 5 is not clean, and the lack of hygiene can cause an unpleasant odor. Thus, it is contemplated that a preferred lateral member 12 will be scented so as to negate the odors and, thereby permit the attending professional to properly concentrate on his or her task.

The lateral member 12 is selectively attachable to at least one longitudinal member 14, and is preferably selectively attachable to a second longitudinal member 16 to secure the lateral member 12 about the pannus 5. The lateral member 12 has a set of first securing means 20 disposed at its distal ends for securing the lateral member 12 to the longitudinal members 14, 16. The first securing means 20 may be mechanical or textile-based, including both cam mechanisms and Velcro®-type closing devices. Alternatively, the first securing means 20 may be disposed on the longitudinal members 14, 16 and slidable thereon for properly securing and tensioning the lateral member 12. It is also contemplated that the first securing means 20 can be attached to neither the lateral member 12 nor the longitudinal member 14, 16, but rather employed as separate devices for securing and restraining the pannus 5 of the patient 1.

In order to maintain the proper tension in the lateral member 12, the longitudinal members 14, 16 are selectively attachable to the table 18 at a second securing means 22, which may be any device that will securely fasten the longitudinal members 14, 16 to the table, including hooks, buttons, loops, clamps, and mechanical or textile devices as described above. As shown in FIG. 1, it may be advisable to locate the arms 3 of the patient 1 such that the lateral member 12 and the longitudinal members 14, 16, restrain them. It is not always the case that the patient 1 will be unconscious during the contemplated procedures, and thus it is important to keep the patient's arms 3 from interfering with the operation of the abdominal restraint and the attending doctor.

In the embodiment of the abdominal restraint 10 shown in FIG. 1, the configuration including the lateral member 12 and the longitudinal member 14, 16 is intended for securing a pannus 5 having a relatively small mass. A heavier pannus 5 would place a significant stress on the lateral member 12, which in turn would displace the lateral members 14, 16 and eventually the pannus 5 would recede over the groin area 7. The present invention, however, is configured to properly restrain a heavier pannus 5 in another series of embodiments shown first in FIG. 2.

Figure 2:
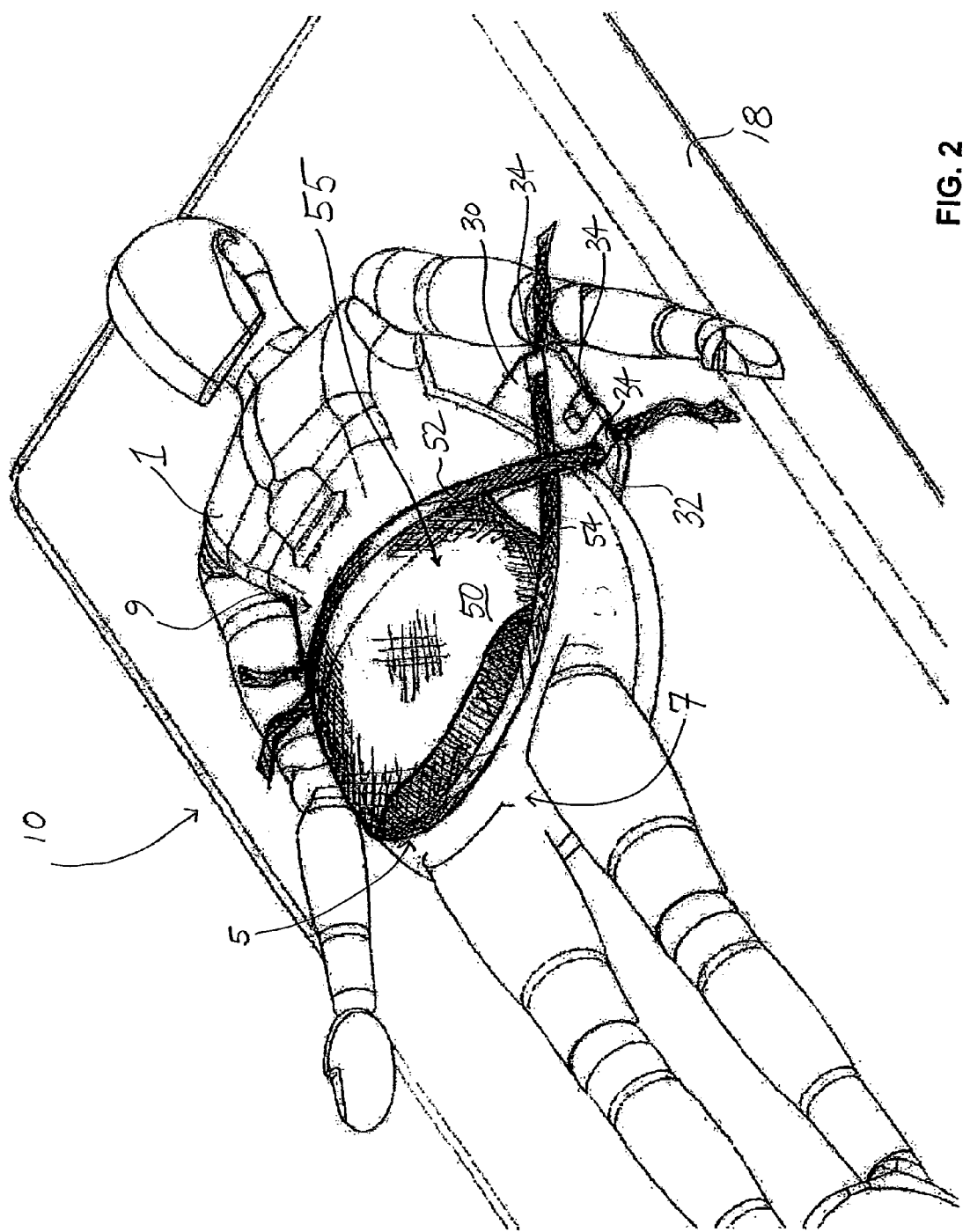
FIG. 2 is a perspective view of an abdominal restraint in accordance with another embodiment of the present invention shown in use on a patient.

FIG. 2 is a perspective view of the present invention according to an alternate embodiment shown in use on a patient 1. As before, the patient 1 is disposed in a prone position on a table 18, with the abdominal restraint 10 of the present invention securing and restraining an abdominal pannus 5. In this embodiment, the abdominal restraint 10 generally includes a base member 30 that is located underneath the patient 1. Also shown is a first flexible band 52 and a second flexible band 54 that are disposed on either side of a contoured web 50. Together, the first flexible band 52, the second flexible band 54, and the contoured web 50 make a support member 55 that is used to secure and restrain the pannus 5.

As shown in FIG. 2, the first flexible band 52 is disposed between the pannus 5 and the torso 9 of the patient 1. The second flexible band 54 is disposed between the pannus 5 and the groin area 7 of the patient 1. The contoured web 50 is securely affixed to the first flexible band 52 and second flexible band 54 so as to form a single, stable unit for controlling the mass of the pannus 5.

Each component of the support member 55 is both flexible and sterile so as to be usable in surgical conditions. In preferred embodiments, the contoured web 50 is composed of a hypoallergenic and scented synthetic material, such as nylon. The contoured web 50 is also preferably composed of a material that is both breathable and non-radio opaque such that x-rays, CT scans, PET scans, MRI images and other radiological imaging or treatment can take place with the abdominal restraint 10 in place. It is also preferable for the first flexible band 52 and the second flexible band 54 to have similar characteristics, including the scenting, hypoallergenic features and invisibility to radiological processes.

Given the various sizes and shapes of abdomens to which the present invention is suited, it is also preferable for the contoured web 50 to be shaped or curved to better accommodate the mass of the various abdomens. In particular, it is preferred that the contoured web 50 is curved in two perpendicular directions to form a compound curved surface that will better adapt to the contours of the pannus 5. For example, as a typical pannus 5 is more massive on the bottom side near the second flexible band 54, it is preferable for the contoured web 50 to be wider at that junction than at its junction with the first flexible band 52. It is further preferred that the support member 55 be disposable, such that each patient 1 will receive his or her own sterile, scented and hypoallergenic device for each particular procedure.

As shown in FIG. 2, the first flexible band 52 and second flexible band 54 are selectively attached to the base member 30. The base member 30 defines a surface 32 upon which the patient 1 is placed and a plurality of locking mechanisms 34 for receiving and immobilizing the first flexible band 52 and second flexible band 54. It should be understood that the base member 30 could embody a number of equally desirable designs, all of which are usable with the support member 55 of the present invention. The particular embodiments of the base member 30 are discussed below with reference to FIGS. 3 through 9.

Figure 3:
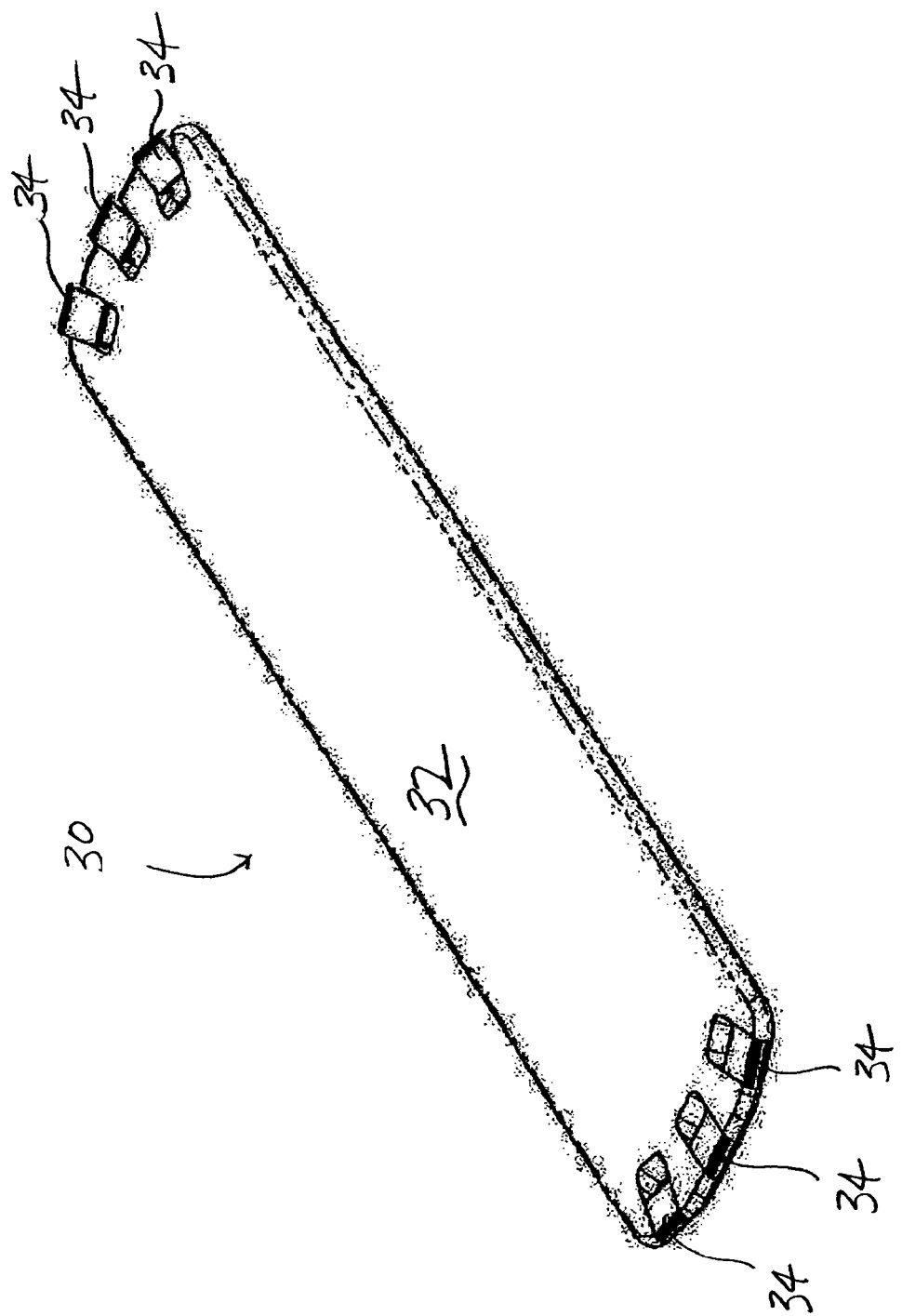
FIG. 3 is a top perspective view of a base member in accordance with the present invention.

Turning to FIG. 3, the base member 30 of FIG. 2 is shown without the patient 1 thereon. The base member 30 defines a surface 32 that is substantially planar and is preferably composed of a synthetic material or plastic that is durable so that it can be sterilized and used repeatedly for different patients using different support members 55. The base member 30 includes a plurality of locking mechanisms 34 that are disposed on the lateral periphery of the surface 32 for receiving and securing portions of the support member 55. In preferred embodiments, the locking mechanisms 34 are cam devices that are simple to use and easy to maintain yet provide sufficient friction to secure a pannus weighing up to 125 pounds (60 kilograms). Additionally, the locking mechanisms 34 should be composed of a synthetic material or plastic that is durable so that it can be sterilized and used repeatedly. The entirety of the base member 30 is preferably non-radio opaque such that it will not interfere with any radiological procedures that the patient must undergo while his or her abdomen is being restrained.

Figure 4:
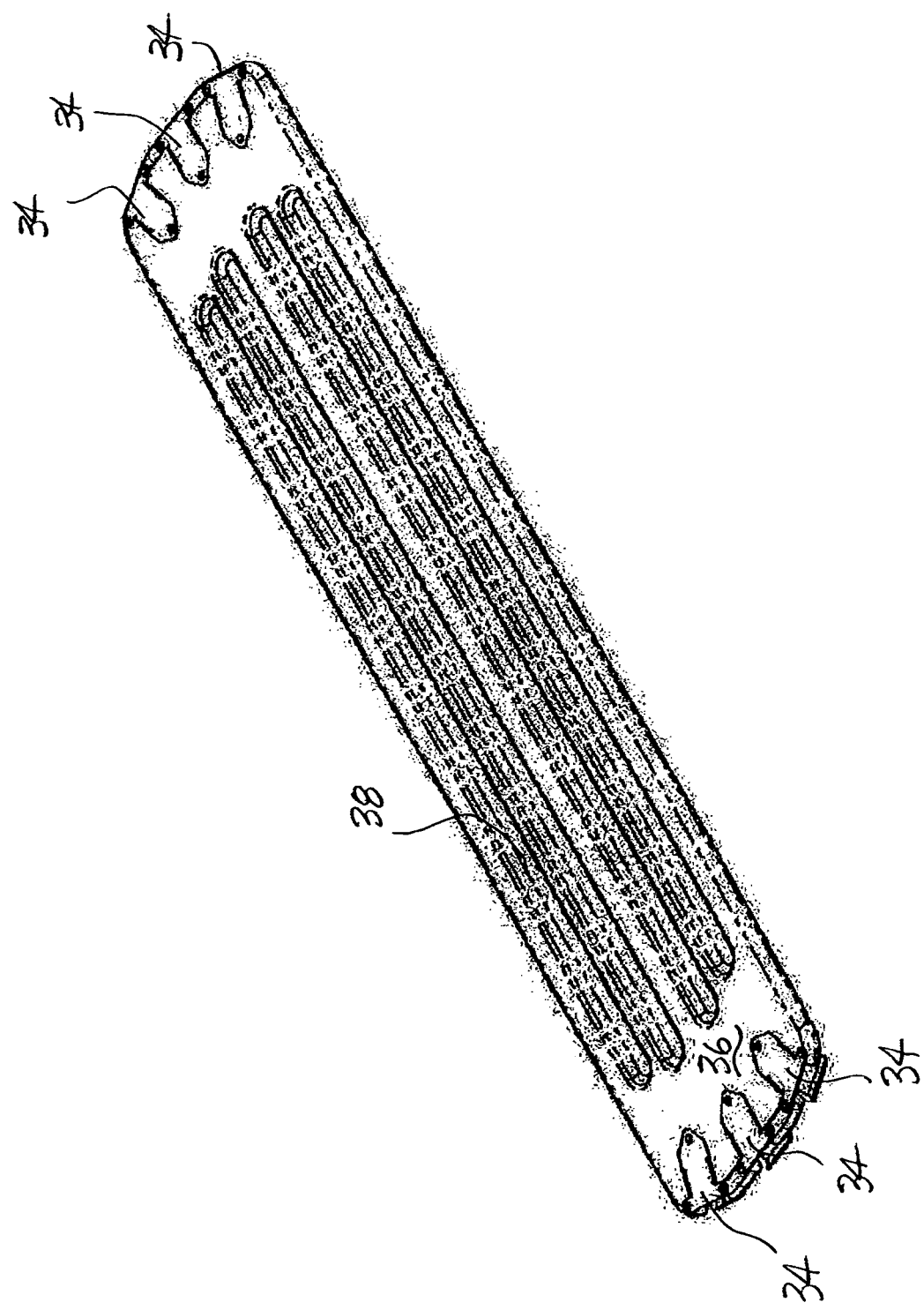
FIG. 4 is a bottom perspective view of a base member in accordance with the present invention.

The base member 30 is shown from a bottom perspective view in FIG. 4. As shown, the base member 30 further defines a second surface 36 that in use is placed against the table 18 shown in FIGS. 1 and 2. The second surface 36 defines a series of depressions 38 that serve a number of purposes, including reducing the overall weight of the base member 30, as well as preventing the base member 30 from sliding along the surface of the table 18. The locking mechanisms 34 described with reference to FIG. 3 are also shown from the bottom perspective view.

Figure 5:
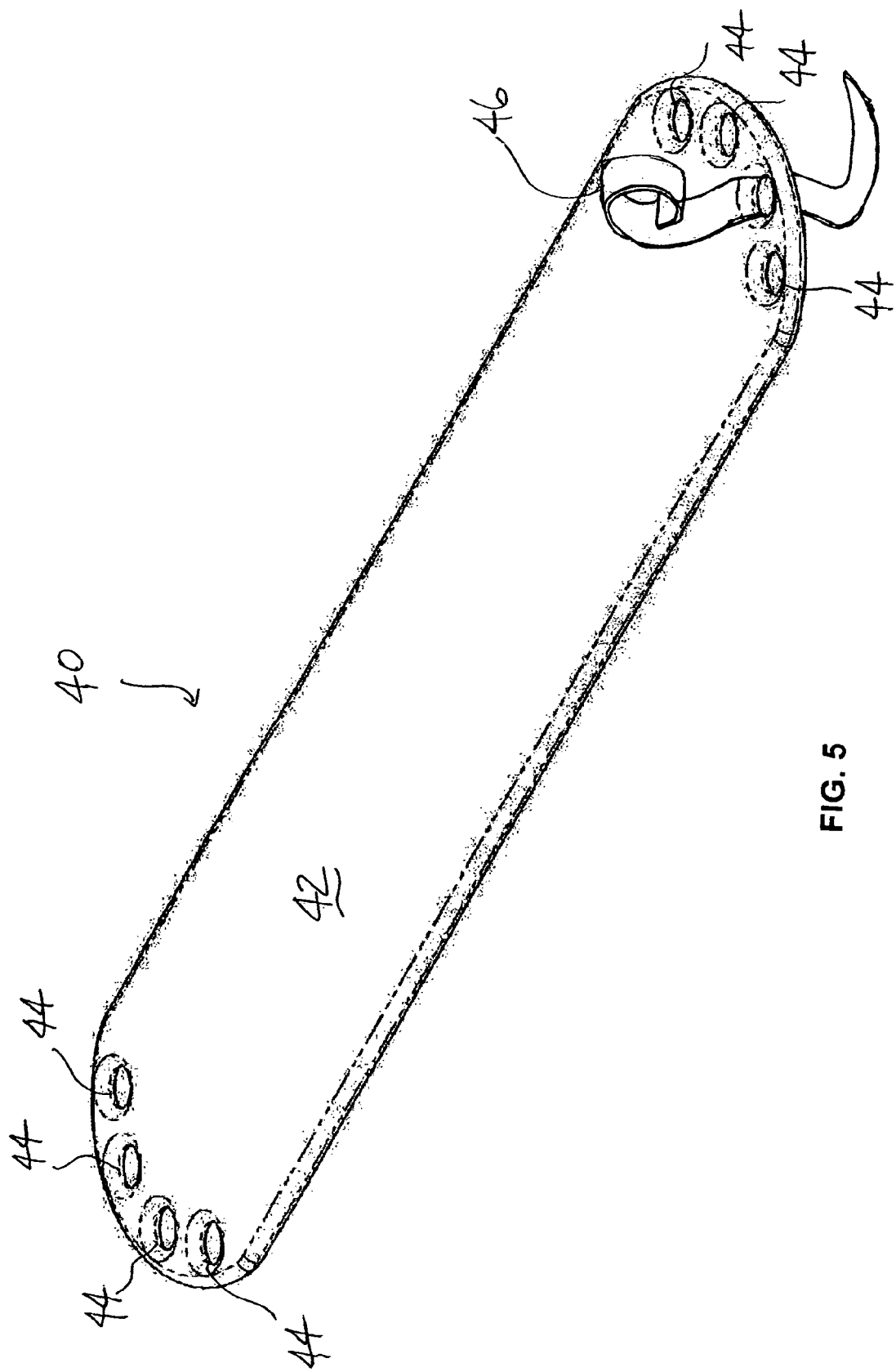
FIG. 5 is a top perspective view of a base member in accordance with an alternate embodiment of the present invention.

FIG. 5 is a perspective view of another base member 40 usable in a alternate embodiment of the present invention. As shown, the base member 40 defines a surface 42 that is substantially planar and preferably composed of a synthetic material or plastic that is durable so that it can be sterilized and used repeatedly for different patients using different support members 55. The base member 40 includes a plurality of openings 44 that are disposed on the lateral periphery of the surface 42 for receiving portions of the support member 55.

As the base member 40 shown in FIG. 5 does not have integrated locking mechanisms, it is contemplated that the first flexible band 52 and second flexible band 54 will have securing means disposed thereon. For example, the base member 40 of the present invention is adapted for use with a support member 55 that has Velcro® disposed on its ends such that the elongated portions, i.e. the first flexible band 52 and the second flexible band 54, can be looped through the openings 44 and self-fastened. The entirety of the base member 40 is preferably non-radio opaque such that it will not interfere with any radiological procedures that the patient must undergo while his or her abdomen is being restrained.

As previously noted, it is common for patients 1 to undergo a vast array of medical procedures while in a conscious or semi-conscious state. For example, a patient 1 is typically awake during an angioplasty, during which a stent or other medical device is threaded through the femoral artery to the patient's heart. In such a case, it is imperative that the patient 1 be immobilized so as not to interfere with the attending surgeon or the support member 55. Accordingly, the base member 40 shown in FIG. 5 is further adapted to receive at least one arm restraint 46 that can be secured to the base member 40 through one of the openings 44 in the manner described above. In a preferred embodiment, the arm restraint 46 will have at least one Velcro® closure for securing it to the base member 40, as well as securing the arms 3 of the patient 1. As there are numerous openings 44 defined in the base member 40, one or more arm restraints 46 are provided at selected intervals along the periphery of the base member 40. The arm restraint 46 is preferably comprised of a material that can be sterilized for use in surgical conditions.

Figure 6:
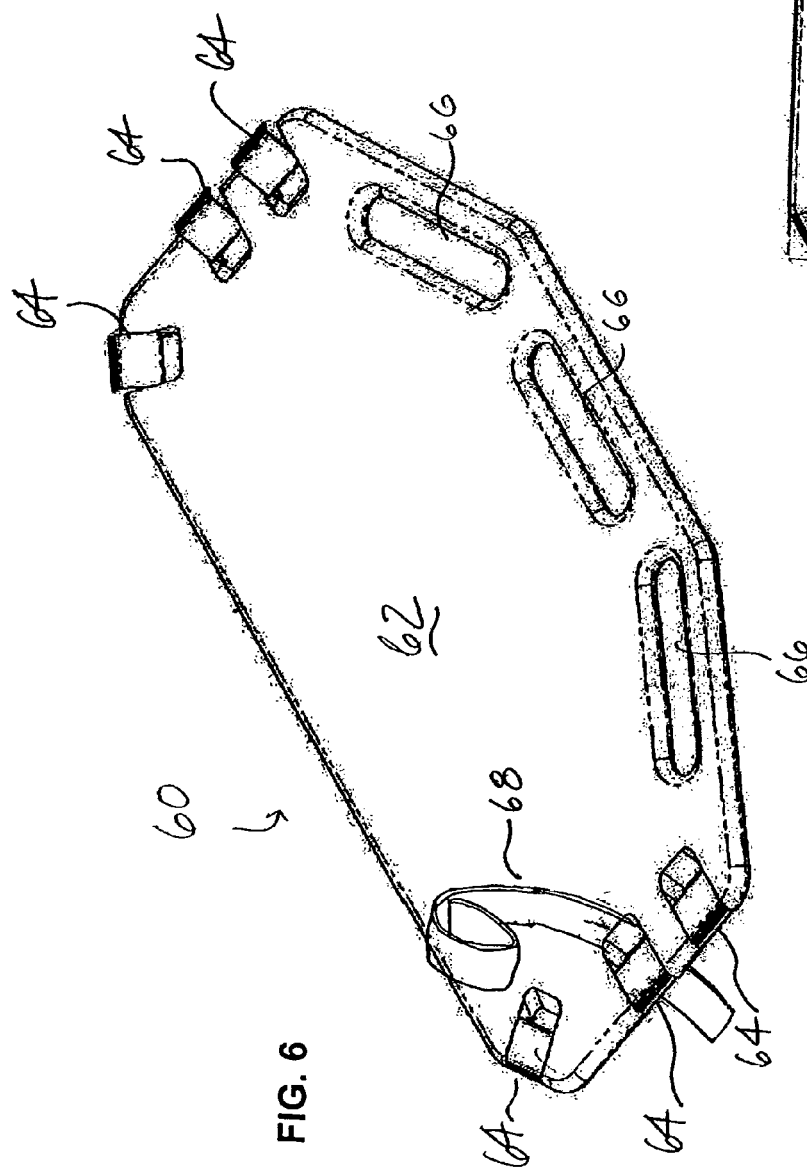
FIG. 6 is a top perspective view of a base member in accordance with an alternate embodiment of the present invention.
Figure 7:
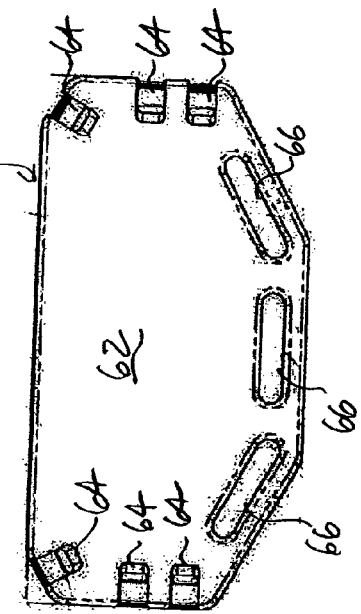
FIG. 7 is a plan view of the base member shown in FIG. 6.

FIG. 6 is a perspective view of another design of a base member 60 in accordance with an alternate embodiment of the present invention. FIG. 7 is a plan view of the base member 60 shown in FIG. 6. In this embodiment, the base member 60 defines a surface 62 that is substantially trapezoidal in shape. A plurality of locking mechanisms 64 similar to those described above is disposed on the lateral periphery of the surface 62. Additionally, the base member 60 shown here includes a plurality of oblong openings 66 that serve as handles for the placement and adjustment of the base member 60. The oblong openings 66 are preferably disposed on the periphery of the surface 62 between the plurality of locking mechanisms 64.

As described above, there is a need for the present invention to incorporate arm restraints to help immobilize the patient 1 during procedures for which he or she is conscious or semi-conscious. To that end, the base member 60 is adapted to receive and secure at least one arm restraint 68 that can be selectively attached to the base member 60 via any one of the locking mechanisms 64. In one embodiment, the arm restraint 68 can be a fabric or synthetic strap that has one end adapted to pass through the locking mechanism 64 and a second end adapted to secure a patient's arm 3. As previously noted, one particular means for securing the patient's arm 3 is to configure the arm restraint 68 to wrap around itself and be secured via a Velcro® or other mechanical closure. It should be understood that the arm restraint 68 described with reference to FIGS. 6 and 7 is equally well suited for use with the base member shown in FIGS. 3 and 4. Preferably, the arm restraint 68 is sterile or can be sterilized and re-used in surgical conditions.

Figure 8:
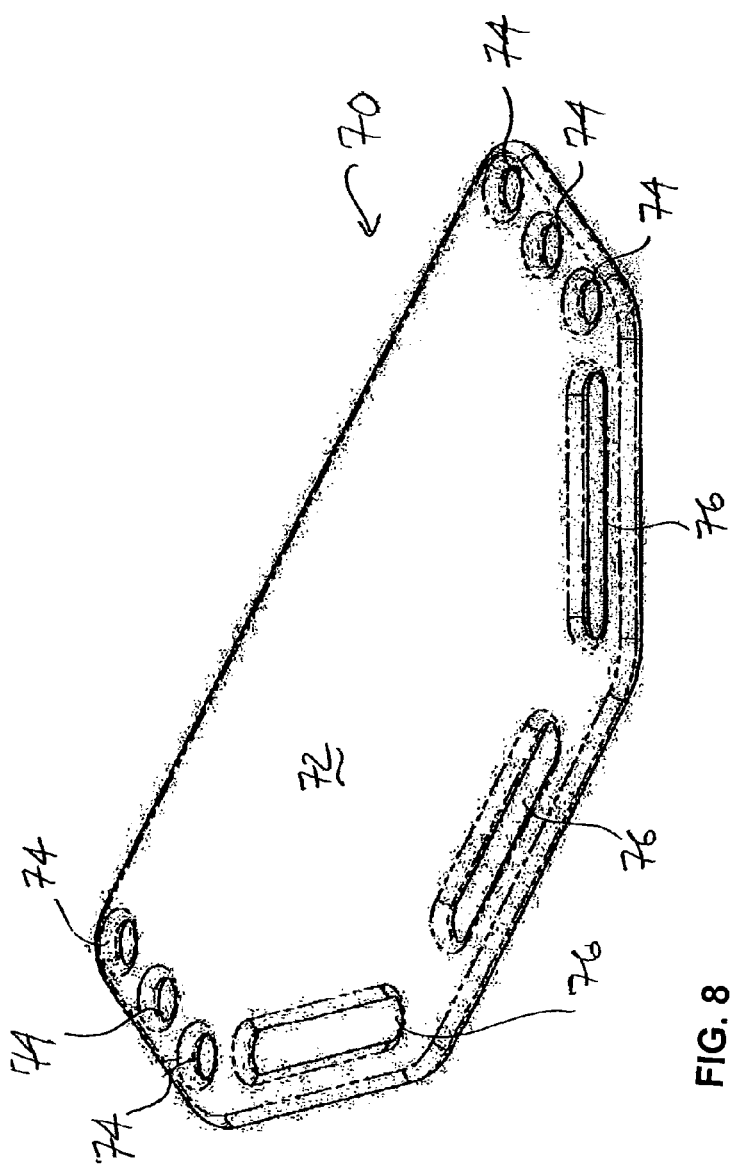
FIG. 8 is a top perspective view of a base member in accordance with an alternate embodiment of the present invention.
Figure 9:
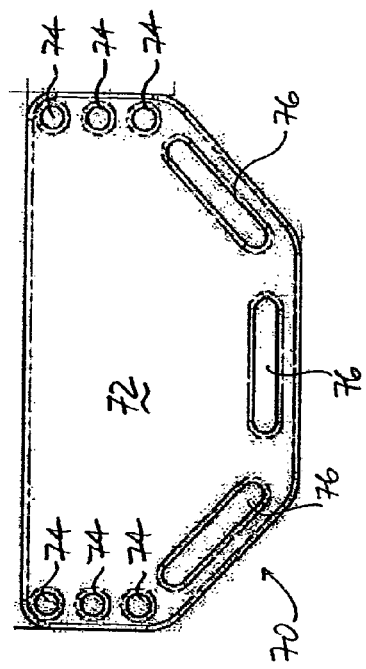
FIG. 9 is a plan view of the base member shown in FIG. 8.

FIG. 8 is a perspective view of another design of a base member 70 in accordance with an alternate embodiment of the present invention. FIG. 9 is a plan view of the base member 70 shown in FIG. 8. In this embodiment, as in the one previously described, the base member 70 defines a surface 72 that is substantially trapezoidal in shape. Unlike the previous embodiment, a plurality of openings 74 similar to those described above is disposed on the lateral periphery of the surface 72. The base member 70 shown here includes a plurality of oblong openings 76 that serve as handles for the placement and adjustment of the base member 70. The oblong openings 76 are preferably disposed on the periphery of the surface 72 between the pluralities of openings 74. It should be understood that the base member 70 shown in FIGS. 8 and 9 is also adapted for use with the arm restraints described with reference to FIG. 5.

As described herein, the present invention embodies a number of different designs that are adaptable for use over a range of situations ranging from gynecological exams to open-heart surgery. For example, it is possible to use the abdominal restraint 10 of the present invention in embodiments that include the longitudinal members or the base member. Likewise, there are several designs of the base member that enable the user to select whether to use arm restraints, where to place any arm restraints, and how to most efficiently secure the support member to the base member. As previously noted, the first embodiment of the present invention is most useful for a pannus that is relatively light. Alternatively, for the more massive pannus, it would be advisable to use an abdominal restraint that incorporates the base member, the support member, and the plurality of locking mechanisms to properly confine the pannus.

The present invention provides the physician or surgeon with a number of options for approaching the heretofore-unsolved problems associated with medical procedures on obese patients. Although the present invention has been described with reference to numerous embodiments, the foregoing description is intended to be merely illustrative. Numerous other arrangements and configurations can be readily devised by those skilled in the art without departing from the spirit and scope of the present invention as defined by the following claims.

We claim:

1. An abdominal restraint comprising:
    a base member defining a central region upon which a patient can be positioned; and
    a support member comprising:
        a first band configured to extend across an abdominal region of the patient from one side of the patient to the other between the patient's pannus and groin;
        a second band configured to extend across an abdominal region of the patient from one side of the patient to the other between the patient's pannus and torso;
        a web disposed between the first and second bands, the web defining a central portion configured to be secured about the pannus of the patient's abdomen to displace and restrain the pannus away from the patient's groin area,
    the support member selectively attachable to the base member, the base member including a plurality of openings through which the support member may be secured, and wherein the central portion is curved in two perpendicular directions to form a compound curved surface configured to contour to the pannus and accommodate the bulk of the pannus.

2. The abdominal restraint of claim 1 wherein the support member is non-radio opaque.

3. The abdominal restraint of claim 1 wherein the central portion is comprised of a sterile flexible material.

4. The abdominal restraint of claim 1 wherein the base member includes a plurality of locking mechanisms for securing the support member.

5. The abdominal restraint of claim 4 wherein the plurality of locking mechanisms comprises a plurality of cams for securing the support member.

6. The abdominal restraint of claim 1 further comprising an arm restraint selectively connected to the base member.

7. The abdominal restraint of claim 1 wherein the support member is scented.

8. A medical abdominal restraint for supporting and displacing a pannus of an individual thereby exposing the groin, the restraint comprising:
    a sterile flexible band configured to extend across an abdominal region of the patient from one side of the patient to the other and for positioning between the pannus and the groin in a prone patient;
    a second sterile flexible band configured to extend across an abdominal region of the patient from one side of the patient to the other and for positioning between the pannus and the torso of the prone patient;
    a contoured web disposed between the first and second sterile flexible bands and having a contoured surface to accommodate the pannus, wherein the contoured surface is curved in two perpendicular directions to form a compound curved surface configured to contour to the pannus, and wherein the pannus is supported and displaced; and
    means for securing and tensioning the sterile flexible bands when positioned between the pannus and the groin to displace and thereby expose the groin, the means for securing and tensioning the sterile flexible bands including a base member to which the sterile flexible bands may be selectively attached, and the base member including a plurality of locking mechanisms for securing and tensioning the sterile flexible bands, and wherein the plurality of locking mechanisms comprises a plurality of cams for securing the sterile flexible bands.

9. The medical abdominal restraint of claim 8 wherein the contoured web is comprised of a sterile material.

10. The medical abdominal restraint of claim 8 wherein the contoured web is scented.

11. The medical abdominal restraint of claim 8 further comprising an arm restraint connected to the base member.

* * * * *

UNITED STATES PATENT AND TRADEMARK OFFICE
CERTIFICATE OF CORRECTION

PATENT NO. : 7,938,121 B2
APPLICATION NO. : 11/056044
DATED : May 10, 2011
INVENTOR(S) : John McKnight et al.

It is certified that error appears in the above-identified patent and that said Letters Patent is hereby corrected as shown below:

On the Title Page

Item (73), Column Assignee reads, "Merit Medical Systems, Inc., south Jordan, UT (US)" which should read, "John McKnight, Morgantown, WV (US)"

Signed and Sealed this
Thirteenth Day of August, 2013

Teresa Stanek Rea
*Acting Director of the United States Patent and Trademark Office*